(12) United States Patent
Vajda et al.

(10) Patent No.: US 10,654,772 B2
(45) Date of Patent: May 19, 2020

(54) SELECTIVE OXIDATIVE DEHYDROGENATION OF PROPANE TO PROPYLENE

(71) Applicant: UCHICAGO ARGONNE, LLC, Chicago, IL (US)

(72) Inventors: Stefan Vajda, Lisle, IL (US); Avik Halder, Clarendon Hills, IL (US); Larry A. Curtiss, Downers Grove, IL (US)

(73) Assignee: UCHICAGO ARGONNE, LLC, Chicago, IL (US)

(*) Notice: Subject to any disclaimer, the term of this patent is extended or adjusted under 35 U.S.C. 154(b) by 0 days.

(21) Appl. No.: 16/128,105

(22) Filed: Sep. 11, 2018

(65) Prior Publication Data
US 2020/0079709 A1    Mar. 12, 2020

(51) Int. Cl.
*C07C 5/48* (2006.01)
*B01J 23/72* (2006.01)
*B01J 21/18* (2006.01)
*C07C 11/06* (2006.01)

(52) U.S. Cl.
CPC ............ *C07C 5/48* (2013.01); *B01J 21/18* (2013.01); *B01J 23/72* (2013.01); *C07C 11/06* (2013.01); *C07C 2521/18* (2013.01); *C07C 2523/72* (2013.01)

(58) Field of Classification Search
CPC ............ C07C 5/42–48; C07C 2521/18; C07C 2523/72; C07C 11/06; B01J 21/18; B01J 23/72
See application file for complete search history.

(56) References Cited

U.S. PATENT DOCUMENTS

| 8,143,189 B2 | 3/2012 | Vajda | |
| 2009/0233790 A1* | 9/2009 | Vajda | B01J 23/42 502/334 |
| 2018/0297914 A1* | 10/2018 | Aljundi | C07C 5/48 |

OTHER PUBLICATIONS

Piyush Chaturbedy, et al., "Oxidative Dehydrogenation of Propane over a High Surface Area Boron Nitride Catalyst: Exceptional Selectivity for Olefins at High Conversion," ACS OMEGA 2018, 3, pp. 369-374.
Stefan Vajda, et al., Subnanometre platinum clusters as highly active and selective catalysts for oxidative dehyrdrogenation of propane, Feb. 2009, DOI:10.1038/nmat2384, 27 pages.
Yizhong Lu et al., "One-Pot Synthesis, Photoluminescence, and Electrocatalytic Properties of Subnanometer-Sized Copper Clusters", 2011, 133 (7), pp. 2060-2063.

* cited by examiner

*Primary Examiner* — Ali Z Fadhel
(74) *Attorney, Agent, or Firm* — Cherskov Flaynik & Gurda, LLC

(57) ABSTRACT

The invention provides a method for generating alkenes, the method having the steps of contacting an alkane with catalyst clusters no greater than 10 nm for a time sufficient to convert the alkane to alkene.

19 Claims, 7 Drawing Sheets

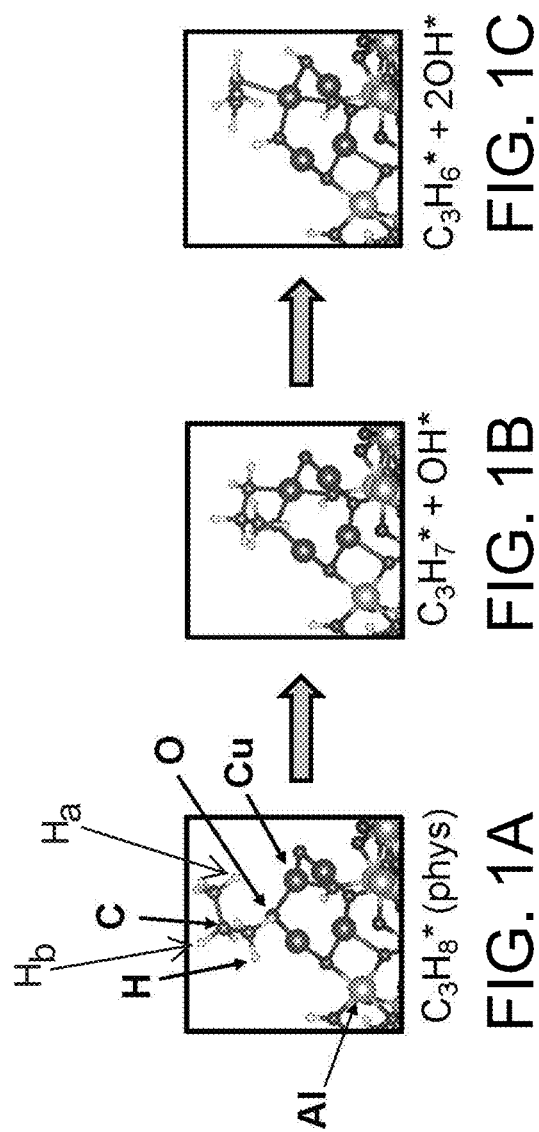

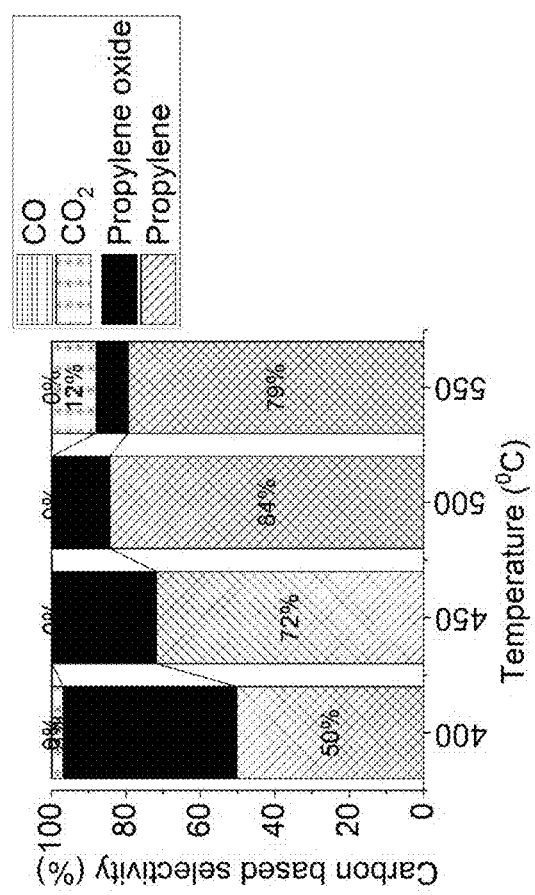
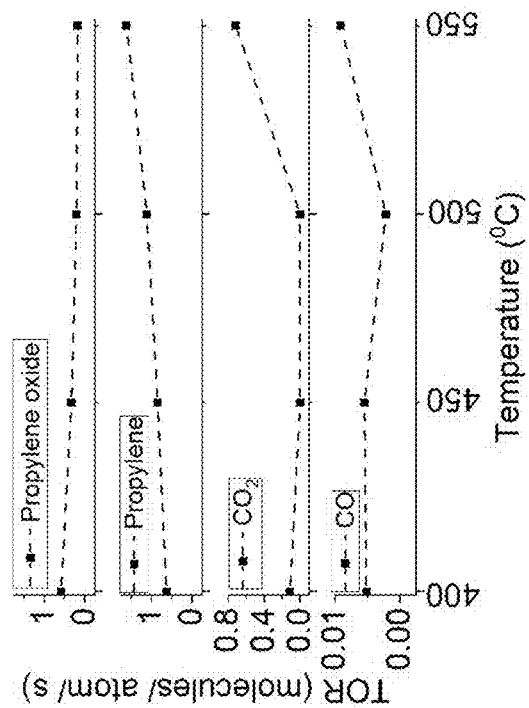
FIG. 2B
FIG. 2A

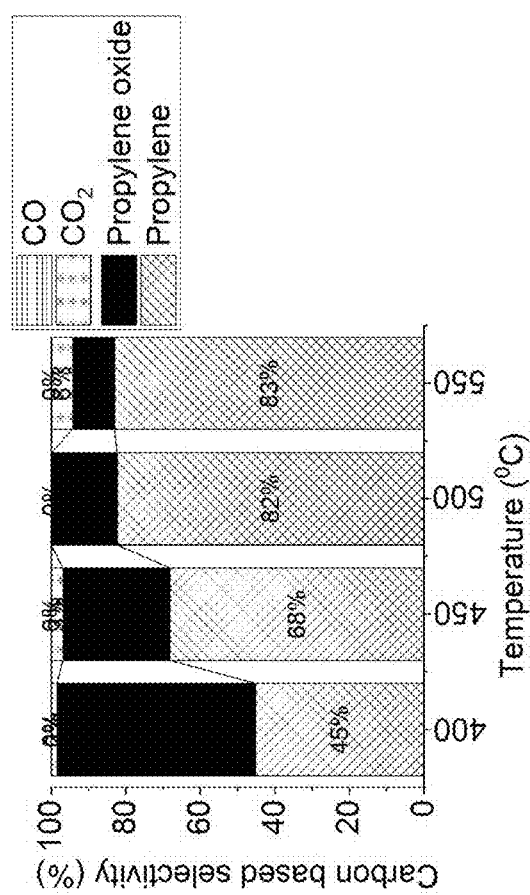
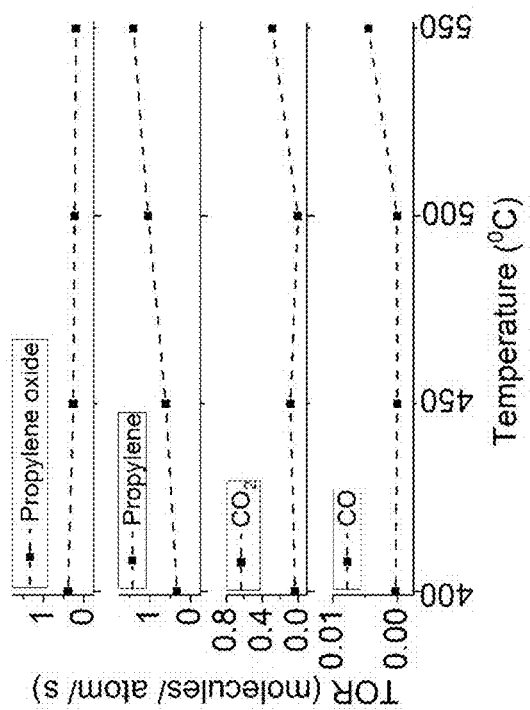
FIG. 3B
FIG. 3A

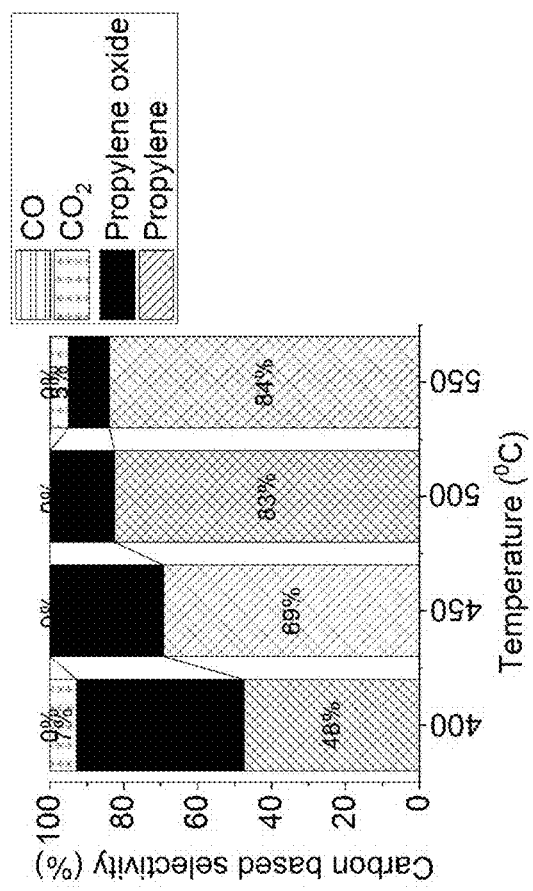
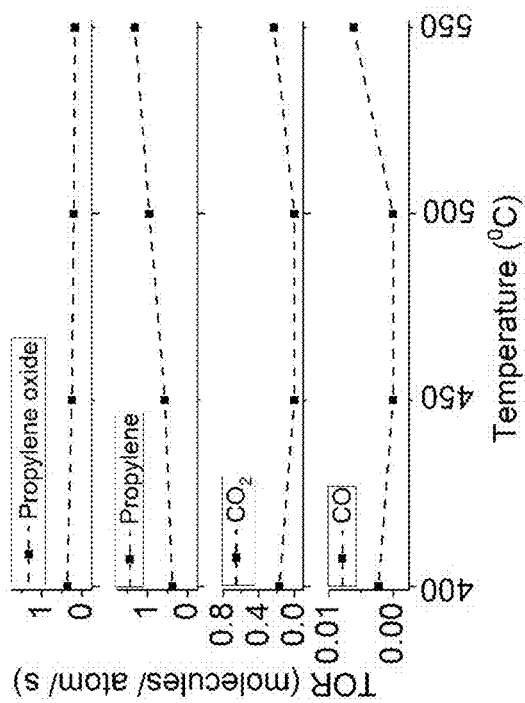
FIG. 4B
FIG. 4A

SELECTIVE OXIDATIVE DEHYDROGENATION OF PROPANE TO PROPYLENE

CONTRACTUAL ORIGIN OF THE INVENTION

This invention was made with government support under Contract No. DE-AC02-06CH11357 awarded by the United States Department of Energy to UChicago Argonne, LLC, operator of Argonne National Laboratory. The government has certain rights in the invention.

BACKGROUND OF THE INVENTION

1. Field of the Invention

This invention relates to dehydrogenation processes and more specifically, this invention relates to a system and method for dehydrogenating alkanes to alkenes.

2. Background of the Invention

Natural gas is full of light paraffins such as methane, ethane, propane and butane, which can contribute in different reactions to produce valuable olefinic products. However, catalyst coking occurs (e.g., when platinum catalysts are used) due to the necessary high temperatures involved in the endothermic processes utilized. As such, some form of catalyst regeneration is required. Other problems associated with endothermic processes are the high energy demand, complexity of controlling temperatures and the possibility of reaction runaway.

Oxidative dehydrogenation (ODH) of propane due to its exothermic nature, low operative temperature, and minimal coke deposition is a promising alternative to endothermic industrial dehydrogenation reactions. A model for ODH reactions is depicted below in Equation 1.

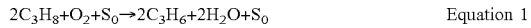

$$2C_3H_8 + O_2 + S_0 \rightarrow 2C_3H_6 + 2H_2O + S_0 \quad \text{Equation 1}$$

where $S_0$ is the active site of the catalyst.

However, current catalysts that produce propylene from propane using energetically favorable ODH routes suffer from low selectivity, low activity, or both. Metal oxide based catalysts (e.g., $VO_x$) suffer from poor activity. Also, some state of the art catalysts (e.g., platinum) used for ODH are expensive and therefore not viable for industrial applications. Platinum cluster catalysts also suffer from poor stability at operating temperatures and thus need to be stabilized by complex overcoating techniques. This is technologically challenging and simultaneously could partially deactivate the catalyst. Moreover, platinum catalysts tend to combust to produce carbon dioxide under oxidative conditions.

A need exists in the art for a system and method for producing propylene directly from propane. The system and method should eliminate coking and any side reactions associated with state of the art high temperature protocols. Also, the system and method should be a simple protocol to generate target olefin with high activity and selectivity.

SUMMARY OF INVENTION

An object of the invention is to provide a method and system for converting alkanes to alkenes that overcomes many of the drawbacks of the prior art.

Another object of the invention is to provide a system and method for efficiently producing alkenes from alkanes. A feature of the invention is that different types of alkanes can be treated, including a branched (e.g. 2-methyl propane), linear (ethane, propane, butane etc.) and cyclic alkanes (cyclopentane, cyclohexane etc.). Another feature is that the invention can be used for the selective activation of the C—H bond in general in conversion processes that include the removal of a hydrogen from the feedstock, including in methane. (Conversion of methane is of very high importance. The critical step is the activation of the C—H bond as the first step to form longer chain or other products.) An advantage of the invention is minimization of waste and unwanted carbon oxides. Another advantage of the invention is that the presence of molecular oxygen within the reaction mixture helps in driving the dehydrogenation reaction exothermally, and also helps preventing the deactivation of the catalyst due to coking.

Still another object of the invention is to provide a system and method for directly converting propane to propylene. A feature of the invention is utilizing subnanometer clusters of copper and/or palladium and/or bimetallic copper-palladium clusters. An advantage of the invention is the use of relatively inexpensive metals at low loadings.

Yet another object of the invention is to provide a system and method for dehydrogenating alkanes. A feature of the invention is the use of catalyst clusters wherein each of the clusters comprise no more than 30 atoms. An advantage of the invention is that the uncoordinated nature of the atoms results in the catalyst conferring high selectivity and high activity toward the target alkenes. This selectivity and activity can be tuned by modifying the catalyst composition and atom numbers.

Briefly, the invention provides a method for generating alkenes, the method comprising contacting alkane with catalyst clusters no greater than 30 for a time sufficient to convert the alkane to alkene.

BRIEF DESCRIPTION OF DRAWING

The invention together with the above and other objects and advantages will be best understood from the following detailed description of the preferred embodiment of the invention shown in the accompanying drawings, wherein:

FIGS. 1A-C show a schematic diagram of the propane-cluster interaction, in accordance with features of the present invention;

FIG. 2A is a graph of turn-over rates for various molecules when 4-atom Cu clusters are utilized in dehydrogenation, in accordance with features of the present invention;

FIG. 2B is a bar chart of selectivities of the various molecules featured in FIG. 2A, in accordance with features of the present invention;

FIG. 3A is a graph of turn-over rates for various molecules when 12-atom Cu clusters are utilized in dehydrogenation, in accordance with features of the present invention;

FIG. 3B is a bar chart of selectivities of the various molecules featured in FIG. 3A, in accordance with features of the present invention;

FIG. 4A is a graph of turn-over rates for various molecules when 20-atom Cu clusters are utilized in dehydrogenation, in accordance with features of the present invention;

FIG. 4B is a bar chart of selectivities of the various molecules featured in FIG. 4A, in accordance with features of the present invention;

DETAILED DESCRIPTION OF THE INVENTION

Figure 5B:
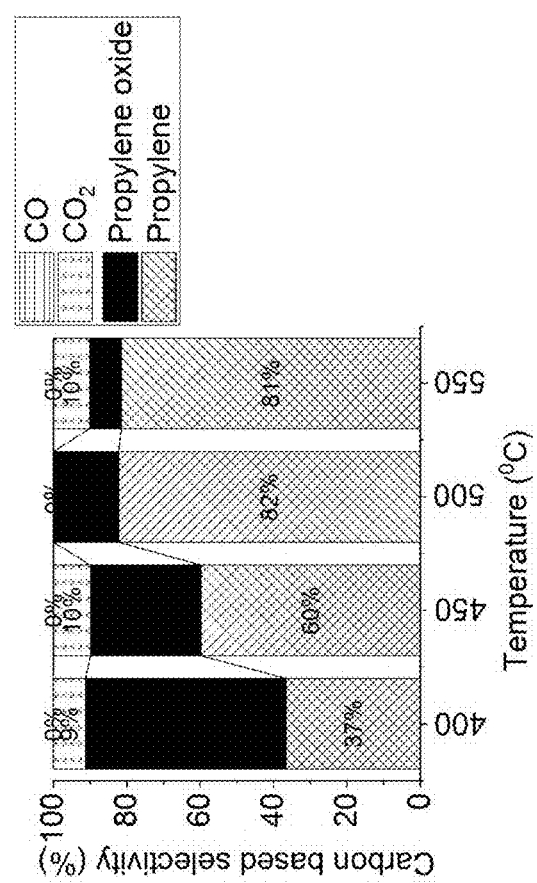
FIG. 5B is a bar chart of selectivities of the various molecules featured in FIG. 5A, in accordance with features of the present invention.

The foregoing summary, as well as the following detailed description of certain embodiments of the present invention, will be better understood when read in conjunction with the appended drawings.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

The following detailed description should be read with reference to the drawings in which similar elements in different drawings are numbered the same. The drawings, which are not necessarily to scale, depict illustrative embodiments and are not intended to limit the scope of the invention.

As used herein, an element or step recited in the singular and preceded with the word "a" or "an" should be understood as not excluding plural said elements or steps, unless such exclusion is explicitly stated. As used in this specification and the appended claims, the term "or" is generally employed in its sense including "and/or" unless the content clearly dictates otherwise.

Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

This invention provides a system and method for dehydrogenating alkanes to alkenes. The alkanes may be n-alkanes (such as ethane, propane, butane etc.), branched alkanes, and cyclic alkanes (such as cyclohexane). The invention also enables the selective activation of C—H bond in general in conversion processes that includes the removal of a hydrogen from a feedstock. The critical step is the activation of the C—H bond as the first step to form longer chain or other products.

A salient feature of the invention is the use of clusters comprising mono- and/or bimetallic catalysts to directly convert propane to propylene oxide in the presence of oxygen. It is noteworthy that the relevant clusters are not nanoclusters or nanoparticles with typically ordered structures, rather, clusters less than 10 nm that have disordered structures or structures made of smaller subunits, building blocks. In light of the foregoing, suitable clusters are typically less than 10 nm, preferably between approximately 0.1 nm and 9 nm in diameter and most preferably between 0.2 nm and 2 nm in diameter.

These small clusters can serve as model catalytically active sites with a large fraction of undercoordinated, thus potentially highly active, sites.

An embodiment comprises a subnanometer cluster based mono- and bimetallic catalysts made of Cu and Pd that produces propylene directly from propane with high activity and selectivity. The invention leverages the temperature-dependent catalytic properties of the metal-oxide film-supported monometallic Cu and Pd clusters, as well as bimetallic Cu—Pd clusters.

Metal oxide supports may include those selected from the group consisting of alumina, iron-oxide, silica oxide, zeolites, titanium oxide, zinc oxide, zirconium oxide, tin oxide, magnesium oxide, including their combinations. Carbon based supports selected from the group consisting of nanocrystalline diamond, graphite, amorphous carbon various forms and compositions of graphene may also be utilized, including their combinations. These supports may be modified with oxygen, nitrogen, hydrogen and metal dopants. The supports may define planar or nonplanar surfaces or loose aggregate such as powders.

Ultimately, the supports are exposed to a gas mixture containing propane and oxygen, the latter even at trace amounts (e.g., between 100 ppm and 1000 ppm), at near atmospheric pressure.

At temperatures starting at about 400° C., the cluster-based process produces propylene at a high rate (up to about 1.6 propylene molecules produced per cluster metal atom per second at 550° C.), with high selectivity (about 80 percent). From the studied Cu, Pd and CuPd cluster compositions, monometallic Cu clusters were found possessing the highest activity as well as selectivity in both propylene oxide and propylene production. Theoretical calculations support the experimentally observed high activity and selectivity of the best performing $Cu_4$ clusters.

FIGS. 1A-C show a schematic depiction of the interaction between alkanes and the afore-described clusters. FIG. 1A depicts physisorbed propane on a $CuO_4$ cluster. Propane is shown bound to an oxygen of the cluster.

FIG. 1B shows the complex with a loss of a first hydrogen $H_a$. As such, the intermediate $C_3H_7$ is depicted as bound to the cluster.

FIG. 1C shows the substrate cluster complex, wherein a second hydrogen $H_b$ has been lost from the alkane substrate. As such, propene is depicted as bound to the cluster.

Reaction Conditions

Detail

Dehydrogenation of propane occurs over different size metal clusters. Reactant gas may comprise pure propane (i.e., neat with typical impurities), or else in a carrier gas. Typical impurities may include oxygen, water vapor, nitrogen, and carbon dioxide. Temperature of the conversion ranges from 400° C. and 550° C. Between temperature steps of 50° C., a slow heating/cooling is applied to assure thermal stabilization. Suitable pressures are from 0.01 atm to 20 atm.

Conversion may be facilitated by using ultraviolet, visible or infrared light to promote dehydrogenation thermophotochemically. In these instances, the light is applied to the conversion process during removal of the hydrogens (See FIGS. 1A-C) with heat not exceeding 500° C. Alternatively, radiation may be applied to promote the removal of the hydrogens that are hard to remove thermally. The degree of heating during this radiation application is determined empirically.

Feedstream components can vary and may be comprised of promoters. The presence of possible promoters, such as co-fed water, hydrogen, CO, $CO_2$, $N_2O$, $H_2O_2$, $O_3$, and combinations thereof can be used to further increase efficacy.

Catalyst Preparation

Detail

Small clusters (those containing less than about 30 atoms) comprise catalytically active sites with a large fraction of undercoordinated, thus potentially highly active, sites. These features along with the strong charge transfer with the support material and cluster's fluxionality confers the clusters with features not present within its bulk analog.

A myriad of elemental metals, their alloys and compounds may serve as catalyst material, including but not limited to Cu, Ag, Au Co, Fe, Mo, Pd, Pt, Ti, V, W, their oxides and carbides, and combinations thereof.

The catalysts are prepared by softly landing the clusters which are produced in a molecular beam within a high vacuum chamber on an ALD coated substrate (e.g. alumina) on $SiO_2$/n-type (P-doped) Si wafer. The clusters are so landed that the impact energy is less than 1 eV per atom which ensures that the clusters stay intact and does not undergo fragmentation or pinning onto the substrate. Soft landing protocols are described in U.S. Pat. No. 8,143,189 B2, issued to the applicant, and incorporated in its entirety herein.

Alternatively, cluster distributions may be prepared by wet methods, such as those methods described in, Yizhong Lu, Wei Chen, and Shaowei Chen *J. Am. Chem. Soc.,* 2011, 133 (7), pp 2060-2063, the entirety of which is incorporated herein by reference.

Rigid substrates may be metal oxide selected from the group consisting of aluminum oxide, iron oxide, silicium oxide, zeolites, titanium oxide, zinc oxide, zirconium oxide, tin oxide, magnesium oxide, cerium oxide and combinations thereof. The substrate could be further doped with alkali metals. The clusters-catalysts themselves could be doped with alkali atoms as well.

Example 1

Clusters within two spots of 8 mm diameter were deposited on the top of n-doped silicon wafers coated with a thin layer of alumina. The alumina layer, of about 3 monolayer (ML) thickness, was fabricated by atomic layer deposition. The metal loading of the $Cu_4$, $Cu_{12}$, $Cu_{20}$, $Pd_4$, $Cu_4Pd$, and $Cu_3Pd$ samples was 16.2 ng, 16.2 ng, 16.2 ng, 27.2 ng, 18.4 ng, and 19.00 ng respectively, corresponding to a surface coverage of 10 percent of an atomic monolayer equivalent. This ensures the inter-cluster distance of approximately 5-10 nm and inhibits any sintering occurring during the reaction as the catalyst is heated.

The reaction was performed in situ with X-ray characterization to simultaneously monitor the reaction products formation on a mass spectrometer, and to monitor the changes in the oxidation state of the clusters during the course of the reaction. The reactor was maintained at a pressure of 800 Torr with a continuous 18.54 sccm flow of no more than 3 percent $O_2$ and 3 percent propane mixed in helium carrier gas. Other gases can serve as carriers, as long as they are unreactive with the alkanes being transformed. In summary of this point, argon, nitrogen, helium and mixtures thereof are suitable carriers.

Turnover rate (TOR) is defined as the number of product molecules formed per atom of the catalyst per second. TOR for propylene production (number of propylene molecules formed per metal atom of the cluster per second reached about 1.5 at 550° C.

FIG. 2A depicts the TOR for propylene, propylene oxide, CO, and $CO_2$ for neat 4-atom copper clusters ($Cu_4$). FIG. 2B depicts the carbon based selectivity for the reaction products for the 4-atom clusters.

FIG. 3A depicts the TOR for propylene, propylene oxide, CO, and $CO_2$ for neat 12-atom copper clusters ($Cu_{12}$). FIG. 3B depicts the carbon based selectivity for the reaction products for 12-atom clusters.

FIG. 4A depicts the TOR for propylene, propylene oxide, CO, and $CO_2$ for neat 20-atom copper clusters ($Cu_{20}$). FIG. 4B depicts the carbon based selectivity for the reaction products for 20-atom clusters.

The TORs obtained for the larger Cu clusters featured in FIGS. 3A-B and 4A-B ($Cu_{12}$, and $Cu_{20}$ atoms) are comparable to those observed for $Cu_4$ clusters. This relaxes the specific size requirement for high activity of the catalysts, therefore providing a means for large scale production using alternative techniques, including catalysts prepared by "wet-chemistry."

Example 2

Figure 5A:
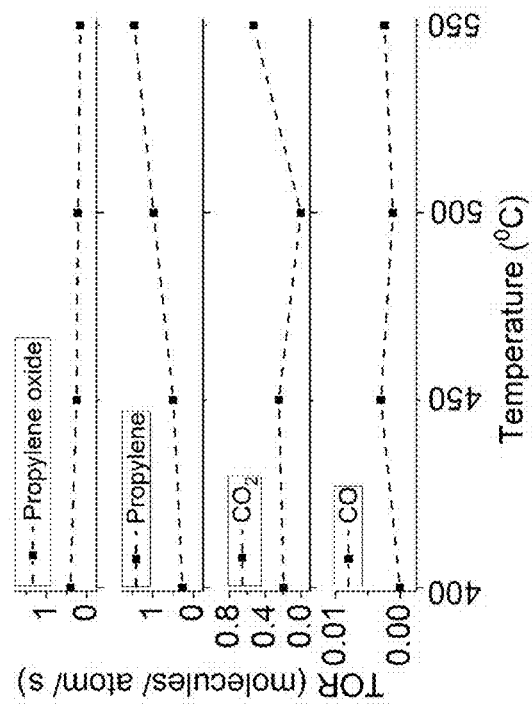
FIG. 5A is a graph of turn-over rates for various molecules when bimetallic 3-atom Cu/1-atom Pd clusters are utilized in dehydrogenation, in accordance with features of the present invention.
Figure 6B:
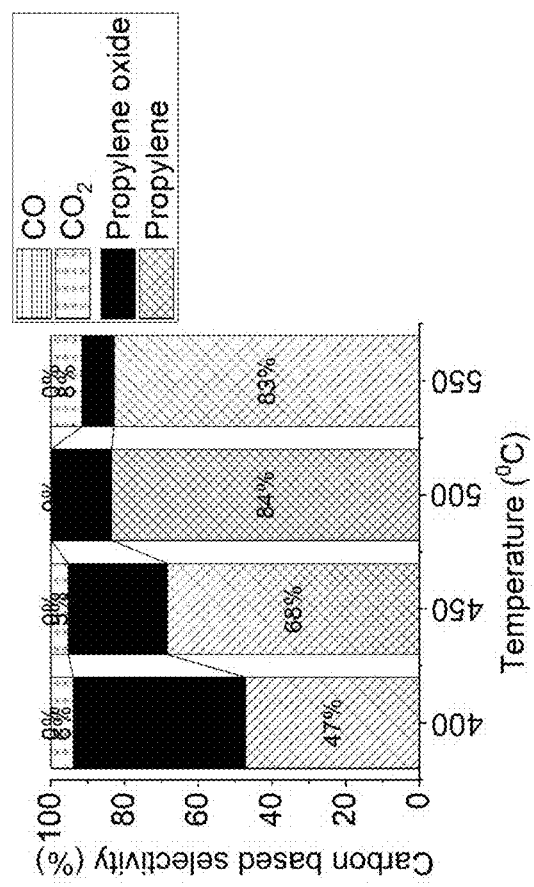
FIG. 6B is a bar chart of selectivities of the various molecules featured in FIG. 6A, in accordance with features of the present invention.
Figure 6A:
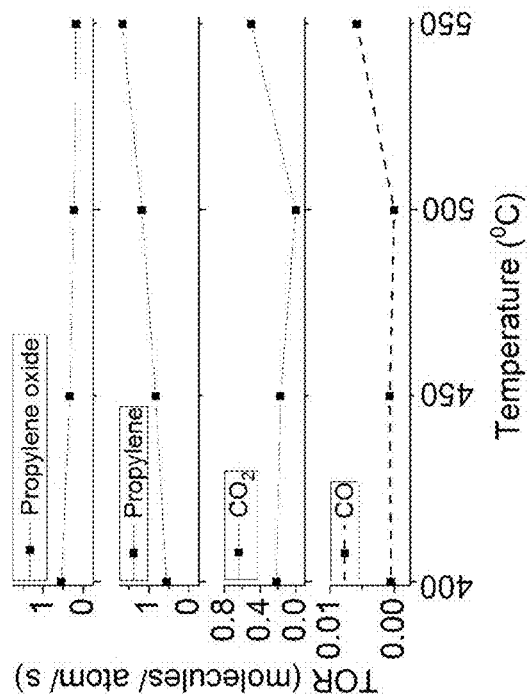
FIG. 6A is a graph of turn-over rates for various molecules when bimetallic 4-atom Cu/1-atom Pd clusters are utilized in dehydrogenation, in accordance with features of the present invention.

FIGS. 5-6 depict the formation of propylene per metal catalyst atom for 3-atom copper, 1-atom palladium clusters (FIG. 5A) and for 4-atom copper, 1-atom palladium clusters (FIG. 6A). Carbon based selectivity for the reaction products are plotted for the Cu3Pd (FIG. 5B) and Cu4Pd (FIG. 6B) catalysts.

Figure 7B:
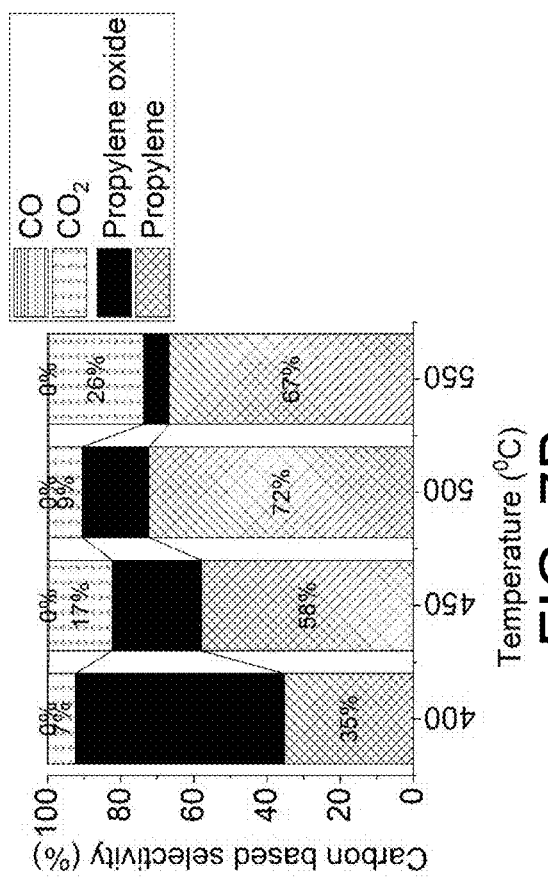
FIG. 7B is a bar chart of selectivities of the various molecules featured in FIG. 7A, in accordance with features of the present invention.
Figure 7A:
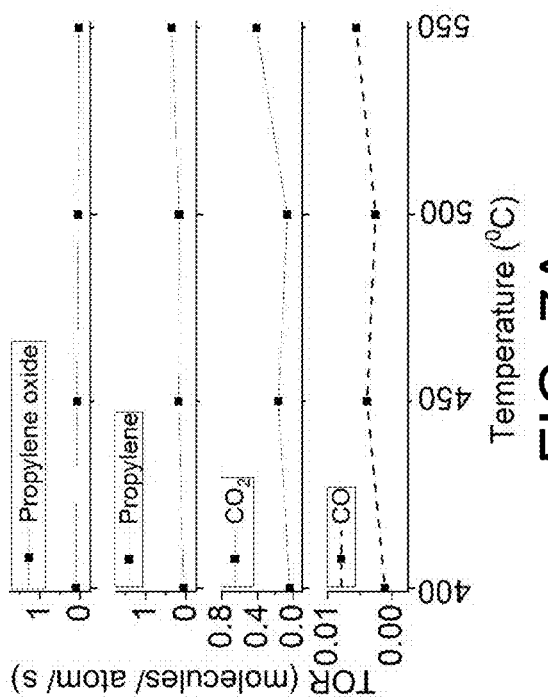
FIG. 7A is a graph of turn-over rates for various molecules when 4-atom Pd clusters are utilized in dehydrogenation, in accordance with features of the present invention.

FIG. 7A is a graph of turn-over rates for various molecules when 4-atom Pd clusters are utilized in dehydrogenation, in accordance with features of the present invention. FIG. 7B is a bar chart of selectivities of the various molecules featured in FIG. 7A, in accordance with features of the present invention It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting, but are instead exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

The embodiment of the invention in which an exclusive property or privilege is claimed is defined as follows:

1. An efficient method for generating alkenes, the method comprising contacting alkane with catalyst clusters no greater than 30 atoms for a time sufficient to convert the alkane to alkene, wherein the atoms are metal, and wherein conversion occurs thermophoto-chemically with ultraviolet or visible wavelength radiations.

2. The method as recited in claim 1 wherein the atoms are metals selected from the group consisting of copper, palladium, platinum, silver, gold, cobalt, and combinations thereof.

3. The method as recited in claim 1 wherein the catalyst clusters are positioned between 5 to 10 nm apart from each other.

4. The method as recited in claim 1 wherein the catalytic clusters are supported by rigid substrate.

5. The method as recited in claim 4 wherein the rigid substrate is a metal oxide selected from the group consisting of aluminum oxide, iron-oxide, silica oxide, zeolites, titanium oxide, zinc oxide, zirconium oxide, tin oxide, magnesium oxide, cerium oxide and combinations thereof.

6. The method as recited in claim 4 wherein the rigid substrate is a carbon based support selected from the group consisting of nanocrystalline diamond, graphite, amorphous carbon, graphene, and combinations thereof.

7. The method as recited in claim 1 wherein the catalytic clusters are deposited on a powder.

8. The method as recited in claim 7 wherein the powder is fluidized.

9. The method as recited in claim 1 wherein the method is conducted in a reaction vessel and the alkane is entrained in a carrier gas flowing through the vessel.

10. The method as recited in claim 9 wherein the carrier gas is an inert gas selected from the group consisting of nitrogen, argon, helium, and combinations thereof.

11. The method as recited in claim 1 wherein the method is conducted at ambient pressure.

12. The method as recited in claim 1 wherein the method is conducted at pressures ranging from between about 0.01 atm and 20 atm.

13. The method as recited in claim 1 wherein the method is conducted at temperatures between about 400° C. and 550° C.

14. The method as recited in claim 1 wherein propylene is generated from propane and no residual intermediates exist.

15. The method as recited in claim 1 wherein the alkane is a compound less than 20 carbons selected from the group consisting of linear alkanes, cyclic alkanes, branched alkanes, and combinations thereof.

16. The method as recited in claim 1 wherein conversion occurs at temperatures not exceeding 500 C.

17. The method as recited in claim 1 wherein the alkane is propane and the alkene is propylene.

18. The method as recited in claim 17 wherein the selectivity for propylene is at least 50 percent at reaction temperatures of between about 400° C. and 550° C.

19. The method as recited in claim 17 wherein propylene is generated from propane without any intermediate reaction steps.

* * * * *